US012642858B2

(12) United States Patent
Yang et al.

(10) Patent No.: US 12,642,858 B2
(45) Date of Patent: Jun. 2, 2026

(54) LONG-LASTING HYDROGEL FOR USE AGAINST DRUG-RESISTANT BACTERIA AND PREPARATION METHOD AND USE THEREOF

(71) Applicant: Zhejiang University, Hangzhou (CN)

(72) Inventors: Geng Yang, Hangzhou (CN); Yuyao Lu, Hangzhou (CN); Kaichen Xu, Hangzhou (CN); Huayong Yang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 442 days.

(21) Appl. No.: 18/132,978

(22) Filed: Apr. 11, 2023

(65) Prior Publication Data

US 2023/0381325 A1     Nov. 30, 2023

(30) Foreign Application Priority Data

May 27, 2022     (CN) .......................... 202210592222.1

(51) Int. Cl.
| | |
|---|---|
| *A61K 47/58* | (2017.01) |
| *A61K 47/46* | (2006.01) |
| *A61K 47/54* | (2017.01) |

(52) U.S. Cl.
CPC .............. *A61K 47/58* (2017.08); *A61K 47/46* (2013.01); *A61K 47/548* (2017.08)

(58) Field of Classification Search
None
See application file for complete search history.

(56) References Cited

U.S. PATENT DOCUMENTS 5,141,973 A * 8/1992 Kobayashi ................. C08J 3/03
524/495

FOREIGN PATENT DOCUMENTS

| | | | | |
|---|---|---|---|---|
| CN | 107987439 A | | 5/2018 | |
| CN | 108283727 A | | 7/2018 | |
| CN | 110467735 A | * | 11/2019 | .............. C08J 3/075 |
| CN | 110694102 A | | 1/2020 | |
| CN | 110755678 A | | 2/2020 | |
| CN | 113637183 A | | 11/2021 | |
| WO | 2021100045 A1 | | 5/2021 | |

OTHER PUBLICATIONS

Dumitrescu (What is honey? Dec. 23, 2020). (Year: 2020).*
Adelnia et al. (Freeze/Thawed polyvinyl alcohol hydrogels: Present, paste and future, European Polymer Journal, vol. 164, Feb. 5, 2022). (Year: 2022).*
Mokhtari er al. (Recent advances in honey-based hydrogels for wound healing applications: Toward natural therapeutics, Journal of Drug Delivery Science and Technology 66 (2021) (Year: 2021).*
Elephchem (PVA dissolution methods, Aug. 30, 2021) (Year: 2021).*
Situ Fangmin, et al., The preparation of PVA/quaternized chitosan compasite hydrogel and its application as artificial dressing for burn wound healing, Functional Materials, 2015, pp. 09133-09143, vol. 9.

* cited by examiner

*Primary Examiner* — Melissa S Mercier
(74) *Attorney, Agent, or Firm* — Ming Jiang; OPENPTO US LLC

(57) ABSTRACT

A long-lasting hydrogel for use against drug-resistant bacteria, and a preparation method and use thereof are provided. In the present disclosure, polyvinyl alcohol (PVA) is mainly adopted as a matrix, and phytic acid and honey including glucose and fructose are added to modify the PVA to obtain the hydrogel. During preparation of the antimicrobial hydrogel, no toxic chemical crosslinking agent or initiator is added, and the antimicrobial hydrogel is mainly obtained by crosslinking PVA, phytic acid, and monosaccharides through ester bonds, hydrogen bonds, and electrostatic adsorption. In addition, the hydrogel obtained by adding phytic acid and honey to the PVA matrix exhibits a significant long-lasting antimicrobial effect for *Staphylococcus aureus* (*S. aureus*), drug-resistant *S. aureus*, and *Pseudomonas aeruginosa* (*P. aeruginosa*), and the antimicrobial effect can last for about 3 months.

12 Claims, 3 Drawing Sheets

*S. aureus*     *drug-resistant S. aureus*     *P. aeruginosa*

*S. aureus*     *drug-resistant S. aureus*     *P. aeruginosa*

1

LONG-LASTING HYDROGEL FOR USE AGAINST DRUG-RESISTANT BACTERIA AND PREPARATION METHOD AND USE THEREOF

CROSS REFERENCE TO THE RELATED APPLICATIONS

This application is based upon and claims priority to Chinese Patent Application No. 202210592222.1, filed on May 27, 2022, the entire contents of which are incorporated herein by reference.

TECHNICAL FIELD

The present disclosure belongs to the field of biological dressings; and the present disclosure relates to a preparation method of an antimicrobial hydrogel, specifically to a long-lasting hydrogel for use against drug-resistant bacteria, and a preparation method and use thereof.

BACKGROUND

Wound dressings have become an important branch within the field of biomedical material research. Wound bacterial infections may cause other diseases and even cause death in severe cases. In the current epidemic of novel coronavirus, bacterial infectious diseases and bacterial infection environments have always threatened the health of people worldwide. Since penicillin was first discovered, antibiotics have become an effective treatment for bacterial infectious diseases. However, the situation is exacerbated due to the increase in bacterial resistance caused by the overuse or improper use of antibiotics. As a result, increasing antimicrobial biomaterials have been developed as substitutes for antibiotics in some cases. Antimicrobial hydrogels have attracted widespread attention due to their advantages such as simple preparation process, structural diversity, and allowed antimicrobial agent loading.

Hydrogels are a group of three-dimensional (3D) network gels formed through chemical or physical crosslinking. Due to superior biocompatibility, controllable physical properties, natural drug-loaded structures, and rich functional groups, hydrogels have gradually become a hot spot in medical wound research. So far, hydrogels have been successfully used to treat skin defects, infected wounds, burn wounds, diabetic feet, in vivo wet wounds, and the like. Depending on different infected wounds, hydrogels need to have excellent tissue adhesion, prominent mechanical properties, and long-lasting antimicrobial activity. Because hydrogels have similar physical and chemical properties such as Young's modulus (0.5 MPa to 1.95 MPa), flexibility, water content (higher than 70%), and air permeability to the skin, hydrogels can provide an antibacterial moist environment for a wound. Currently, there are mainly two antimicrobial modes of hydrogels: 1. An antimicrobial agent such as chitosan or a metal nanoparticle (Ag, Cu, and Zn) is loaded to destroy the cell walls of bacteria. 2. An antimicrobial effect is achieved through an interaction between a physicochemical structure of hydrogel itself and bacteria. The former mode has been maturated, and many studies have confirmed the excellent antimicrobial effect of silver ions. However, the antimicrobial mechanism and antimicrobial effect based on the structure of the material itself are not perfect.

SUMMARY

In order to solve the problems and needs in the background, the present disclosure provides a phytic acid and honey-modified polyvinyl alcohol (PVA)-based antimicrobial hydrogel and a preparation method and use thereof; where the honey and phytic acid are two natural polymer materials and both have excellent hydrophilicity and biocompatibility. Honey is added in the present disclosure. Honey has a pH generally of about 3.2 to 4.5 and most microorganisms and bacteria mainly live in a neutral environment with a pH of 6.5 to 7.5. Such a low pH of honey can also promote the tissue repair. Many ingredients such as sugar, polyphenolic compounds, and hydrogen peroxide in honey contribute to the antimicrobial efficacy of honey. Phytic acid, also known as inositol hexaphosphate, has very rich phosphate groups, and thus can undergo an esterification reaction with PVA, glucose, and other sugars under heating to obtain a tight network structure crosslinked through ester bonds, hydrogen bonds, and electrostatic adsorption. After PVA is modified with honey and phytic acid, the hydrogel can exhibit a prominent antimicrobial effect for *Staphylococcus aureus* (*S. aureus*), drug-resistant *S. aureus*, and *Pseudomonas aeruginosa* (*P aeruginosa*). Therefore, the antimicrobial hydrogel is an organic hydrogel, and is suitable for, but is not limited to, the field of biomedical dressings.

Technical solutions of the present disclosure are as follows:

I. A preparation method of a long-lasting hydrogel for use against drug-resistant bacteria is provided, Including the following steps:

1) Preparation of a hydrogen bond-containing synthetic or semi-synthetic polymer material solution: dissolving a hydrogen bond-containing synthetic or semi-synthetic polymer material in deionized water, and heating and stirring a resulting solution to obtain the hydrogen bond-containing synthetic or semi-synthetic polymer material solution;

2) Preparation of a mixed solution: mixing the hydrogen bond-containing synthetic or semi-synthetic polymer material solution, a phytic acid solution, and honey in a mass ratio of 5:5:2, stirring a resulting solution until the resulting solution is homogeneous and free of impurities, and allowing the solution to stand for bubble removal to obtain a transparent mixed solution;

3) Pre-curing treatment of the mixed solution: pre-curing the mixed solution under heating in an 80° C. water bath until a resulting pre-cured solution is brown and viscous and has a film on a surface thereof, and removing the film to obtain a pre-cured hydrogel solution; and 4) Preparation of an antimicrobial hydrogel: pouring the pre-cured hydrogel solution into a prepared mold, and conducting a plurality of freeze-thaw cycles to obtain a cured hydrogel.

The preparation method further includes the following step:

5) Demolding of the cured hydrogel, after the cured hydrogel is fully cured, taking the fully-cured hydrogel out from the mold, and storing the hydrogel in a refrigerator.

In step 1), the hydrogen bond-containing synthetic or semi-synthetic polymer material solution has a solid content of 10% to 20%; a dissolution temperature is 60° C.; and the stirring is conducted for 24 h at a rotational speed of 800 rpm/min.

In step 2), the phytic acid solution has a mass percentage concentration of 1% to 5%.

In step 2), the honey has a high monosaccharide content, and specifically, glucose and fructose contents in the honey both are greater than 20%.

In step 4), in the freeze-thaw cycles, freeze is conducted at −48° C. for 2 h and thaw is conducted at room temperature for 30 minutes; and three freeze-thaw cycles are adopted.

In step 1), the hydrogen bond-containing synthetic or semi-synthetic polymer material is one or more selected from the group consisting of PVA, polyethylene glycol (PEG), and a cellulose derivative, where the cellulose derivative is specifically selected from the group consisting of carboxymethyl cellulose (CMC) and hydroxypropyl cellulose (HPC), and a mass percentage concentration of the synthetic or semi-synthetic polymer in the hydrogel is 10% to 20%.

II. A long-lasting hydrogel for use against drug-resistant bacteria is provided.

III. A use of the long-lasting hydrogel for use against drug-resistant bacteria in preparation of a skin wound dressing is provided.

The hydrogel of the present disclosure is an antimicrobial hydrogel without any toxic chemical crosslinking agent, and is mainly obtained by adopting PVA as a matrix and compounding the PVA with phytic acid and honey. The traditional PVA hydrogels basically do not have antibacterial activity, and have relatively single structures and relatively poor mechanical properties. After the PVA is modified with phytic acid and honey, the mechanical properties of a resulting hydrogel are greatly improved due to covalent and non-covalent bonding effects such as ester bonds, hydrogen bonds, and electrostatic interactions. In addition, some antibacterial ingredients in the honey exhibit an antimicrobial effect to some degree.

A main antibacterial mechanism of the hydrogel can be illustrated in the following aspects:

(1) Honey has a low pH, which is not conducive to the survival of bacteria.

(2) Concentrations of glucose and fructose in honey are high, and positive charges of these sugars will undergo electrostatic adsorption with negative charges on surfaces of bacteria, thereby destroying cell walls and killing bacteria.

(3) The six phosphate groups of phytic acid will chelate metal ions (mainly $K^+$) in honey, thereby destroying cell walls of bacteria.

(4) The heating during preparation of the hydrogel will promote the increase of hydrogen peroxide in honey, and the hydrogen peroxide has a bactericidal effect and can stimulate the production of vascular endothelial growth factors (VEGFs).

The present disclosure has the following beneficial effects:

The antimicrobial hydrogel of the present disclosure exhibits significant in vitro and in vivo antimicrobial effects for S. aureus, drug-resistant S. aureus, and P. aeruginosa, and can maintain a prominent in vitro antimicrobial effect for drug-resistant S. aureus within three months.

DETAILED DESCRIPTION OF THE EMBODIMENTS

Figure 1:
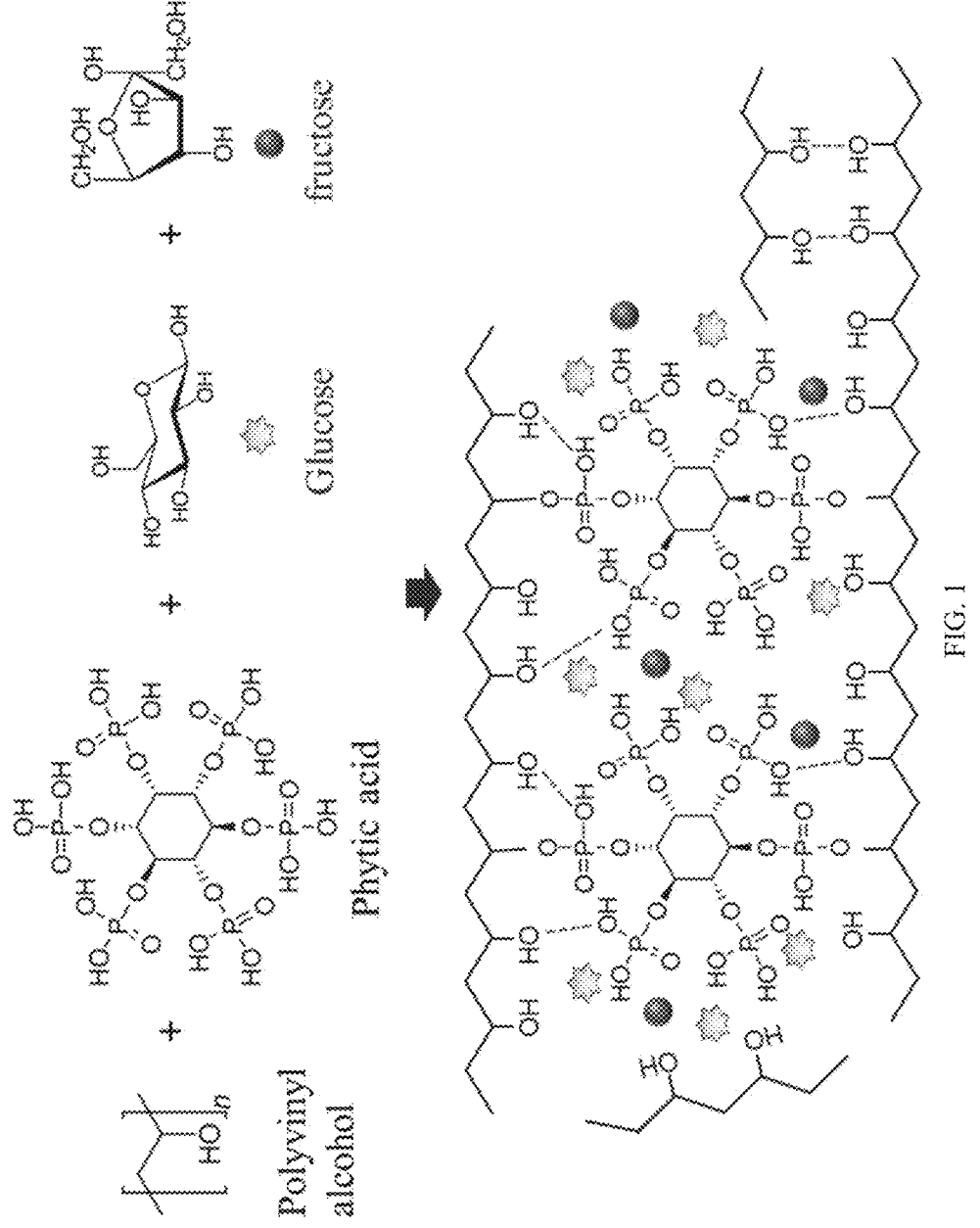
FIG. 1 is a schematic diagram illustrating a structure of the antimicrobial hydrogel based on PVA, phytic acid, and honey.

The present disclosure is described in further detail below with reference to the accompanying drawings and specific examples.

Example 1

1) Preparation of a PVA solution with a solid content of 10%: 1 g of PVA was added to 9 g of deionized water, a resulting mixture was stirred at 60° C. and 800 rpm/min for 24 h to allow dissolution to obtain a transparent and viscous PVA solution, and the PVA solution was stored for later use.

2) Preparation of a mixed solution: 5 g of a phytic acid solution with a mass percentage concentration of 1% and 2 g of honey were added to 5 g of the PVA solution with a solid content of 10%, and a resulting solution was thoroughly stirred at 70° C. and 700 rpm/min until there were no impurities, and then allowed to stand for 0.5 h to remove bubbles to obtain a transparent mixed solution. The vacuum bubble removal method was not adopted here because the viscous solution would cause a large number of bubbles to accumulate on a surface; resulting in difficult bubble removal.

3) Pre-curing treatment of the mixed solution: the mixed solution was pre-cured under heating in an 80° C. water bath for 2 h to obtain a light-brown and viscous pre-cured solution with a film on a surface thereof, and then the film was removed with tweezers to obtain pre-cured hydrogel solution. The film was formed due to the rapid water loss of a surface solution during heating.

4) Preparation of an antimicrobial hydrogel: the pre-cured hydrogel solution was poured into a prepared mold, and three freeze-thaw cycles were conducted to obtain a cured hydrogel, which was elastic.

5) Demolding of the cured hydrogel: after the cured hydrogel was fully cured, the fully-cured hydrogel was taken out from the mold and stored in a refrigerator.

Example 2

1) Preparation of a PVA solution with a solid content of 15%: 1.5 g of PVA was added to 8.5 g of deionized water, a resulting mixture was stirred at 60° C. for 24 h to allow dissolution to obtain a transparent and viscous PVA solution, and the PVA solution was stored for later use.

2) Preparation of a mixed solution: 5 g of a phytic acid solution with a mass percentage concentration of 1% and 2 g of a honey solution were added to 5 g of the PVA solution with a solid content of 15%, and a resulting solution was thoroughly stirred at 70° C. and 700 rpm/min, and then allowed to stand for 0.5 h to remove bubbles to obtain a transparent mixed solution.

3) Pre-curing treatment of the mixed solution: the mixed solution was pre-cured under heating in an 80° C. water bath for 2 h to obtain a light-brown and viscous pre-cured solution with a film on a surface thereof, and then the film was removed with tweezers to obtain pre-cured hydrogel solution.

4) Preparation of an antimicrobial hydrogel: the pre-cured hydrogel solution was poured into a prepared mold and three freeze-thaw cycles were conducted to obtain a cured hydrogel, which was elastic.

5) Demolding of the cured hydrogel: after the cured hydrogel was fully cured, the fully-cured hydrogel was taken out from the mold and stored in a refrigerator.

Example 3

1) Preparation of a PVA solution with a solid content of 20%: 2 g of PVA was added to 8 g of deionized water and a resulting mixture was stirred at 60° C. for 24 h and then stored for later use.

2) Preparation of a mixed solution: 5 g of a phytic acid solution with a mass percentage concentration of 1% and 2 g of a honey solution were added to 5 g of the PVA solution with a solid content of 20% and a resulting solution was thoroughly stirred at 70° C. and then allowed to stand for bubble removal to obtain a transparent mixed solution.

3) Pre-curing treatment of the mixed solution: the mixed solution obtained after the bubble removal was pre-cured under heating in an 80° C. water bath to obtain a light-brown and viscous pre-cured solution with a film on a surface thereof, and then the film was removed with tweezers to obtain a pre-cured hydrogel solution.

4) Preparation of an antimicrobial hydrogel: the pre-cured hydrogel viscous solution was poured into a prepared mold and then freeze-thaw cycles were conducted for curing to obtain an elastic antimicrobial hydrogel.

5) Demolding of the cured hydrogel: after the cured hydrogel was fully cured, the fully-cured hydrogel was taken out from the mold and stored in a refrigerator.

In Examples 1, 2, and 3, a mass concentration of PVA in the antimicrobial hydrogel is changed; because PVA is mainly to serve as a skeleton in the hydrogel, the mass concentration of PVA can be changed to adjust the mechanical properties of the hydrogel. Which can be described specifically as follows: when the concentration of PVA increases from 10% to 20%, the mechanical strength Young's modulus of the antimicrobial hydrogel will increase accordingly. Since an antimicrobial hydrogel is used for human skin, and the excellent elasticity and low mechanical strength of a hydrogel can improve the use comfort, but do not affect the antibacterial activity of the hydrogel, the mass percentage concentration of PVA is preferably 10%.

Figure 2:
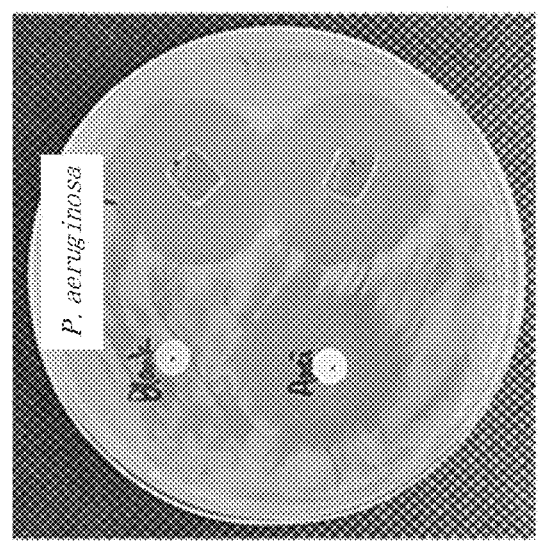
FIG. 2 shows in vitro antimicrobial effects of the antimicrobial hydrogel for S. aureus, drug-resistant S. aureus, and P. aeruginosa after the antimicrobial hydrogel is placed at a constant temperature of 37° C. for 24 h.
Figure 2:
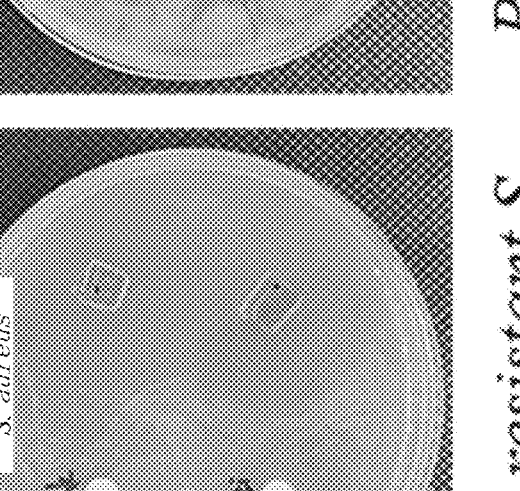
Figure 2:
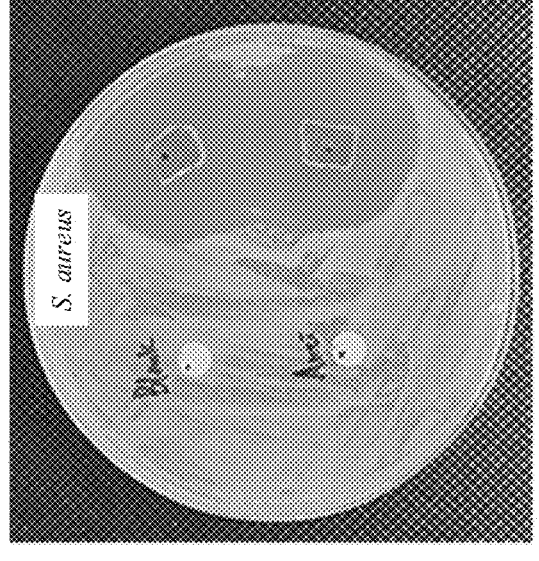
Figure 3:
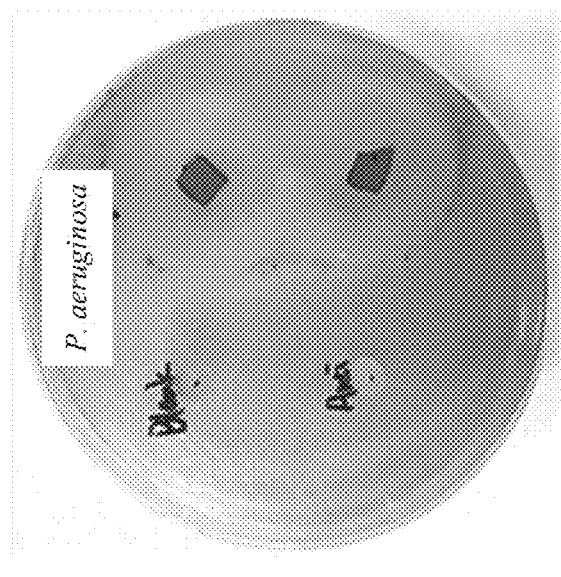
FIG. 3 shows in vitro antimicrobial effects of the antimicrobial hydrogel for S. aureus, drug-resistant S. aureus, and P. aeruginosa after the antimicrobial hydrogel is placed at a constant temperature of 37° C. for three months.
Figure 3:
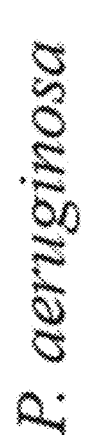
Figure 3:
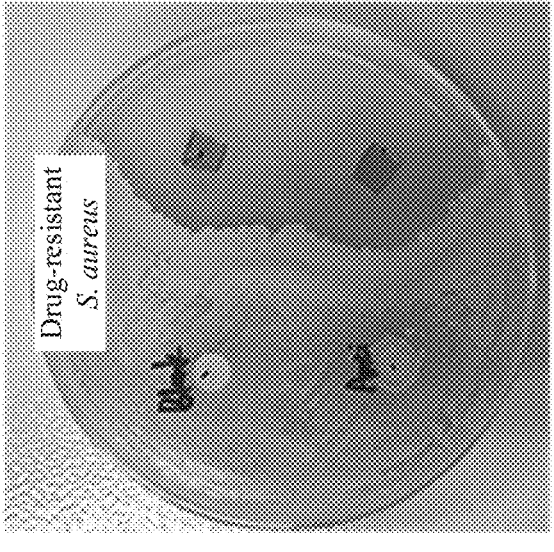
Figure 3:
Figure 3:
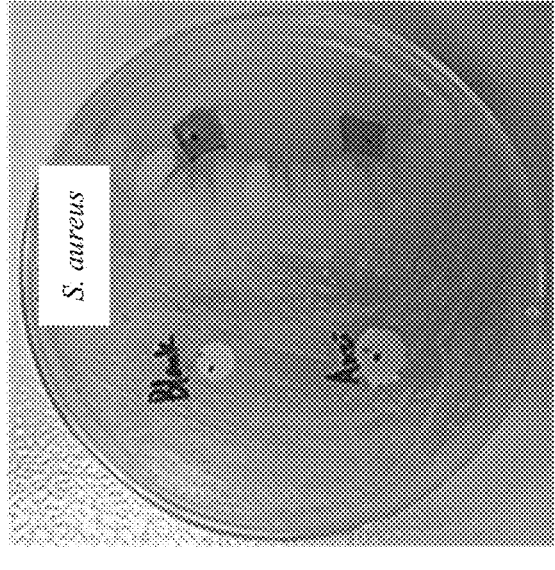

Structures of the antimicrobial hydrogels in Examples 1, 2, and 3 are shown in FIG. 1, and a crosslinked structure of the hydrogel includes covalent ester bonds, non-covalent hydrogen bonds, and electrostatic interactions. In vitro antimicrobial effects of the antimicrobial hydrogel for *S. aureus*, drug-resistant *S. aureus*, and *P. aeruginosa* are shown in FIG. 2, and it can be seen that an inhibitory zone diameter (IZD) of the antimicrobial hydrogel is much larger than an IZD of an antibiotic. The blank in FIG. 2 indicates a blank group and the Anti in FIG. 2 indicates an antibiotic group. FIG. 3 shows antimicrobial effects of the hydrogel in FIG. 2 after being placed for 3 months. It can be seen that, after three months, the bacteria have developed resistance to the antibiotic, but the antimicrobial hydrogel still exhibits a prominent antimicrobial effect. Indicating the durability of antimicrobial activity of the antimicrobial hydrogel of the present disclosure.

IZD data of in vitro antimicrobial activity for an experimental group (mass percentage concentration of phytic acid: 1%), a blank control group, and an antibody group in Example 1 are shown in Table 1, and white filter papers of the control group and the antibody group each have a size of 6 mm.

TABLE 1

IZD data of in vitro antimicrobial activity for an experimental group (mass percentage concentration of phytic acid: 1%), a blank control group, and an antibody group

| Bacterium type | Experimental group (1%) | Control group | Antibody group |
|---|---|---|---|
| *S. aureus* | 10.74 mm | <6 mm | 8.4 |
| Drug-resistant *S. aureus* | 9.5 mm | <6 mm | <6 mm |
| *P. aeruginosa* | 10.6 mm | <6 mm | 10.3 mm |

Example 4

1) Preparation of a PVA solution with a solid content of 10%: 1 g of PVA was added to 9 g of deionized water and a resulting mixture was stirred at 60° C. for 24 h and then stored for later use.

2) Preparation of a mixed solution: 5 g of a phytic acid solution with a mass percentage concentration of 2.5% and 2 g of a honey solution were added to 5 g of the PVA solution with a solid content of 10% and a resulting solution was thoroughly stirred at 70° C. and then allowed to stand for bubble removal to obtain a transparent mixed solution.

3) Pre-curing treatment of the mixed solution: the mixed solution obtained after the bubble removal was pre-cured under heating in an 80° C. water bath to obtain a light-brown and viscous pre-cured solution with a film on a surface thereof, and then the film was removed with tweezers to obtain a pre-cured hydrogel solution.

4) Preparation of an antimicrobial hydrogel: the pre-cured hydrogel viscous solution was poured into a prepared mold and then freeze-thaw cycles were conducted for curing to obtain an elastic antimicrobial hydrogel.

5) Demolding of the cured hydrogel: after the cured hydrogel was fully cured, the fully-cured hydrogel was taken out from the mold and stored in a refrigerator.

IZD data of in vitro antimicrobial activity for an experimental group (mass percentage concentration of phytic acid: 2.5%), a blank control group, and an antibody group in Example 4 are shown in Table 2, and white filter papers of the control group and the antibody group each have a size of 6 mm.

TABLE 2

IZD data of in vitro antimicrobial activity for an experimental group (mass percentage concentration of phytic acid: 2.5%), a blank control group, and an antibody group

| Bacterium type | Experimental group (2.5%) | Control group | Antibody group |
|---|---|---|---|
| *S. aureus* | 12.9 mm | <6 mm | 8.4 |
| Drug-resistant *S. aureus* | 10.7 mm | <6 mm | <6 mm |
| *P. aeruginosa* | 11.5 mm | <6 mm | 10.3 mm |

Example 5

1) Preparation of a PVA solution with a solid content of 10%: 1 g of PVA was added to 9 g of deionized water, and a resulting mixture was stirred at 60° C. for 24 h and then stored for later use.
2) Preparation of a mixed solution: 5 g of a phytic acid solution with a mass percentage concentration of 5% and 2 g of a honey solution were added to 5 g of the PVA solution with a solid content of 10% and a resulting solution was thoroughly stirred at 70° C. and then allowed to stand for bubble removal to obtain a transparent mixed solution.
3) Pre-curing treatment of the mixed solution: the mixed solution obtained after the bubble removal was pre-cured under heating in an 80° C. water bath to obtain a light-brown and viscous pre-cured solution with a film on a surface thereof, and then the film was removed with tweezers to obtain pre-cured hydrogel solution.
4) Preparation of an antimicrobial hydrogel: the pre-cured hydrogel viscous solution was poured into a prepared mold and then freeze-thaw cycles were conducted for curing to obtain an elastic antimicrobial hydrogel.
5) Demolding of the cured hydrogel: after the cured hydrogel was fully cured, the fully-cured hydrogel was taken out from the mold and stored in a refrigerator.

IZD data of in vitro antimicrobial activity for an experimental group (mass percentage concentration of phytic acid: 5%), a blank control group, and an antibody group in Example 5 are shown in Table 3, and white filter papers of the control group and the antibody group each have a size of 6 mm.

TABLE 3

IZD data of in vitro antimicrobial activity for an experimental group (mass percentage concentration of phytic acid: 5%), a blank control group, and an antibody group

| Bacterium type | Experimental group (5%) | Control group | Antibody group |
| --- | --- | --- | --- |
| S. aureus | 15 mm | <6 mm | 8.4 |
| Drug-resistant S. aureus | 11.5 mm | <6 mm | <6 mm |
| P. aeruginosa | 14.5 mm | <6 mm | 10.3 mm |

In Examples 1, 4, and 5, the phytic acid content in the hydrogel is changed, that is, the mass percentage concentration of phytic acid is increased from 1% to 5%. It can be seen from the in vitro antibacterial data in Tables 1 to 3 that the increase of the phytic acid content can increase the IZD of the antimicrobial hydrogel, and this is because the increased mass concentration of phytic acid increases a content of ester bonds and improves a crosslinking density of the hydrogel, thereby destroying the cell walls of bacteria and effectively inhibiting the activity of bacteria.

What is claimed is:

1. A preparation method of a long-lasting hydrogel for use against drug-resistant bacteria, comprising the following steps:
   1) preparation of a polyvinyl alcohol (PVA) solution by dissolving a PVA in deionized water to obtain a first mixture solution, and heating and stirring the first mixture solution to obtain the PVA solution, wherein the heating and stirring in step 1) is conducted at 60° C. for 24 h at a rotational speed of 800 rpm/min;

2) preparation of a mixed solution by mixing the PVA solution, a phytic acid solution, and honey in a mass ratio of 5:5:2 to obtain a second mixture solution, heating and stirring the second mixture solution to promote formation of intermolecular interactions among the PVA solution, the phytic acid solution, and the honey, including ester bonds, hydrogen bonds, and electrostatic interactions, thereby obtaining a third mixture solution, and allowing the third mixture solution to stand for bubble removal to obtain a transparent mixed solution, wherein the phytic acid solution has a mass percentage concentration of 1% to 5%, and the heating and stirring in step 2) is conducted at 70° C. and 700 rpm/min;
   3) pre-curing treatment of the transparent mixed solution by pre-curing the transparent mixed solution under heating in an 80° C. water bath to promote further formation of the intermolecular interactions among the PVA solution, the phytic acid solution, and the honey, including the ester bonds, the hydrogen bonds, and the electrostatic interactions, thereby obtaining a pre-cured hydrogel solution; and
   4) preparation of an antimicrobial hydrogel by pouring the pre-cured hydrogel solution into a prepared mold, and conducting three freeze-thaw cycles to obtain a cured hydrogel.

2. The preparation method of the long-lasting hydrogel for use against drug-resistant bacteria according to claim 1, further comprising the following step:
   5) demolding the cured hydrogel by taking a fully-cured hydrogel out from the mold after the cured hydrogel is fully cured, and storing the fully-cured hydrogel in a refrigerator.

3. The preparation method of the long-lasting hydrogel for use against drug-resistant bacteria according to claim 1, wherein in step 1), the PVA solution has a solid content of 10% to 20%.

4. The preparation method of the long-lasting hydrogel for use against drug-resistant bacteria according to claim 1, wherein the glucose and the fructose content in the honey are both present in an amount greater than 20%.

5. The preparation method of the long-lasting hydrogel for use against drug-resistant bacteria according to claim 1, wherein in step 4), in the freeze-thaw cycles, freezing is conducted at −48° C. for 2 h and thawing is conducted at room temperature for 30 minutes.

6. A long-lasting hydrogel for use against drug-resistant bacteria prepared by the preparation method according to claim 1.

7. A method of preparing a skin wound dressing, comprising the step of providing the long-lasting hydrogel according to claim 6 in a skin wound dressing.

8. The long-lasting hydrogel for use against drug-resistant bacteria according to claim 6, wherein the preparation method of the long-lasting hydrogel for use against drug-resistant bacteria further comprising the following step:
   5) demolding the cured hydrogel by taking a fully-cured hydrogel out from the mold after the cured hydrogel is fully cured and storing the fully-cured hydrogel in a refrigerator.

9. The long-lasting hydrogel for use against drug-resistant bacteria according to claim 6, wherein in step 1), the PVA solution has a solid content of 10% to 20%.

10. The long-lasting hydrogel for use against drug-resistant bacteria according to claim 6, wherein the glucose and the fructose content in the honey are both present in an amount greater than 20%.

11. The long-lasting hydrogel for use against drug-resistant bacteria according to claim 6, wherein in step 4), in the freeze-thaw cycles, freezing is conducted at −48° C. for 2 h and thawing is conducted at room temperature for 30 minutes.

12. A preparation method of a long-lasting hydrogel for use against drug-resistant bacteria, comprising the following steps:

(1) dissolving a PVA in deionized water to obtain a PVA solution;

(2) mixing the PVA solution, a phytic acid solution, and honey in a mass ratio of 5:5:2 to obtain a first mixture solution;

(3) heating and stirring the first mixture solution to promote formation of intermolecular interactions among the PVA solution, the phytic acid solution and the honey, including ester bonds, hydrogen bonds, and electrostatic interactions, thereby obtaining a second mixture solution;

(4) subjecting the second mixture solution to a pre-curing treatment under heating to promote further formation of the intermolecular interactions among the PVA solution, the phytic acid solution, and the honey, including the ester bonds, the hydrogen bonds, and the electrostatic interactions, thereby obtaining a pre-cured hydrogel solution; and (5) pouring the pre-cured hydrogel solution into a mold and performing a freeze-thaw process to obtain a cured hydrogel.

* * * * *